United States Patent [19]

Sano et al.

[11] Patent Number: 5,081,243
[45] Date of Patent: Jan. 14, 1992

[54] PROCESS FOR PRODUCING 3-TETRAZOLYL PYRIDO[1,2-A]PYRIMIDINE DERIVATIVES

[75] Inventors: Atsunori Sano, Saitama; Masami Ishihara; Jun Yoshihara, both of Kawagoe; Hiroyoshi Nawa, Fujimi, all of Japan

[73] Assignees: Wako Pure Chemical Industries, Ltd.; Tokyo, Tanabe Co., Ltd., both of Tokyo, Japan

[21] Appl. No.: 483,191

[22] Filed: Feb. 22, 1990

[30] Foreign Application Priority Data

Feb. 27, 1989 [JP] Japan .................................. 1-46295

[51] Int. Cl.$^5$ .......................................... C07D 239/70
[52] U.S. Cl. ................................. 544/282; 546/276
[58] Field of Search ........................................ 544/282

[56] References Cited

U.S. PATENT DOCUMENTS

| | | | |
|---|---|---|---|
| 4,122,274 | 10/1978 | Juby | 544/282 |
| 4,474,953 | 10/1984 | Wade | 544/282 |
| 4,816,959 | 3/1989 | Matsuishi et al. | 544/282 |

OTHER PUBLICATIONS

Okamoto et al., Chem. Pharm. Bull., 22, 243 (1974).
Journal of Organic Chemistry, vol. 51, No. 15, Jul. 1986, pp. 2988-2994, Washington, D.C., U.S.A.; B. Podanyi et al.: "Nitrogen Bridgehead Compounds 63. Ring-Chain Tautomerism of [(alpha-Azaarylamino)-methylene]Malonitriles".
Journal of American Chemical Society, vol. 80, No. 15, Aug. 1958, pp. 3908-3911, Columbus, Ohio, U.S.; W. G. Finnegan et al.: "An Improved Synthesis of 5-Substituted Tetrazoles".

Primary Examiner—John M. Ford
Assistant Examiner—Jyothsna Venkat
Attorney, Agent, or Firm—Armstrong, Nikaido, Marmelstein, Kubovcik & Murray

[57] ABSTRACT

3-Tetrazolylpyrido[1,2-a]pyrimidin-4-one derivatives useful as an antiallergy agent are produced by reacting a cyano derivative of pyrido[1,2-a]pyrimidin-4-one compound with (i) hydrazoic acid, followed by hydrolysis, or with (ii) a salt of hydrazoic acid, reacting the resulting product with an acid or a base, followed by hydrolysis.

7 Claims, No Drawings

PROCESS FOR PRODUCING 3-TETRAZOLYL PYRIDO[1,2-A]PYRIMIDINE DERIVATIVES

BACKGROUND OF THE INVENTION

This invention relates to a process for producing a 3-tetrazoyl-pyrido[1,2-a]pyrimidin-4-one [] derivative which is useful as an antiallergy agent.

3-Tetrazolyl-pyrido[1,2-a]pyrimidin-4-one derivative represented by the formula:

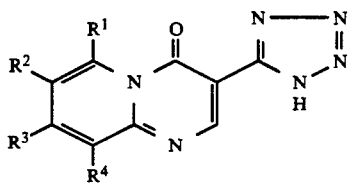

wherein $R^1$ and $R^3$ are independently a hydrogen atom or a lower alkyl group; and $R^2$ and $R^4$ are independently a hydrogen atom, a halogen atom, a lower alkyl group, a phenyl group or

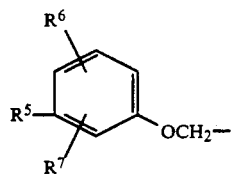

($R^5$ is a hydrogen atom or a hydroxyl group; $R^6$ is a hydrogen atom or an acyl group; and $R^7$ is a hydrogen atom, a lower alkyl group or an allyl group) (hereinafter abbreviated as "compound [I]") and salts thereof are known as drugs having antiallergy activity, and various antiallergy agents containing them as active ingredient have come into wide use.

As a process for producing such a compound, there has most generally been employed a process which comprises reacting a compound of the formula:

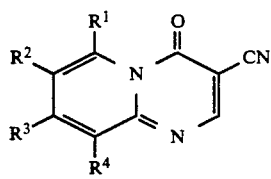

wherein $R^1$ through $R^4$ are as defined above, or the formula:

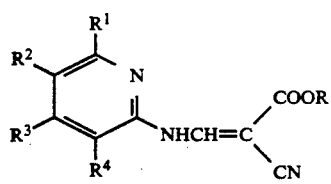

wherein R is a methyl group or an ethyl group; and $R^1$ through $R^4$ are as defined above, with a hydrazoic acid salt of wide variety to carry out conversion to a tetrazole ring, as disclosed, for example, in Japanese Patent Appln. Kokai (Laid-Open) No. 63-246374 and U.S. Pat. Nos. 4,122,274 and 4,816,459. As the hydrazoic acid salt, aluminum azide or ammonium azide is used in the reaction. As described in J. Am. Chem. Soc., 80, 3908-3911 (1958), when sodium azide is used alone in a method for forming a tetrazole ring from a nitrile group, a reaction at a high temperature for a long period of time is required and moreover the yield is low. Therefore, it is considered effective to carry out the conversion to a tetrazole ring by converting sodium azide to ammonium azide, aluminum azide or the like by using ammonium chloride, aluminum chloride or the like together with sodium azide. This method is employed also in the above-mentioned prior art references.

However, even when ammonium chloride, aluminum chloride or the like is thus co-used, the yield is not high by any means, namely, its maximum is a little over 50%, and the co-use of these compounds gives birth to several evils. For example, when ammonium chloride is co-used, sodium azide acts as ammonium azide, which is very highly sublimable and escapes from the system on reaction at a high temperature for a long period of time. Therefore, sodium azide and ammonium chloride should be used in large excess, so that the efficiency is very low. When aluminum chloride or the like is co-used, sodium azide acts as a polyvalent metal salt of hydrazoic acid, such as aluminum azide in the system. The polyvalent metal salt of hydrazoic acid, such as aluminum azide is a very dangerous explosive compound, and therefore its handling requires extreme care and skill. When such a polyvalent metal salt is used in the reaction, a large amount of azide group which does not participate in the conversion to a tetrazole ring remains after the reaction, resulting in generation of a large amount of hydrazoic acid. Therefore, an air pollution problem is caused, and furthermore, disposal of metal wastes due to aluminum, etc. is required.

Accordingly, for making such methods practicable (industrial), there should be considered not only the low yield but also the problem of working environment and assurance of the safety of workers, the problem of facilities for preventing air pollution, the problem of time, labor and the like required for disposal of industrial wastes, etc. Thus, it is very desirable to improve the methods.

SUMMARY OF THE INVENTION

This invention was made in consideration of such conditions and is intended to provide an effective process for producing a compound [I] which is highly safe, hardly involves the problems of air pollution, industrial wastes, etc., and makes it possible to obtain the desired compound [I] easily in high yield.

This invention provides a process for producing a compound of the formula:

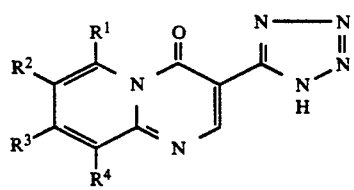

wherein $R^1$ and $R^3$ are independently a hydrogen atom or a lower alkyl group; and $R^2$ and $R^4$ are independently a hydrogen atom, a halogen atom, a lower alkyl group, a phenyl group or

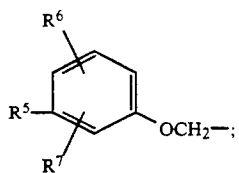

$R^5$ is a hydrogen atom or a hydroxyl group; $R^6$ is a hydrogen atom or an acyl group; and $R^7$ is a hydrogen atom, a lower alkyl group preferably having 1 to 6 carbon atoms or an allyl group, which comprises reacting a compound of the formula:

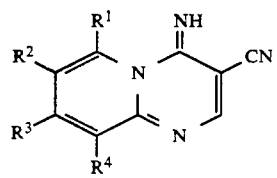

wherein $R^1$ through $R^4$ are as defined above, with (i) hydrazoic acid to obtain the following compound of the formula (II), or (ii) a salt of hydrazoic acid to obtain a compound of the formula:

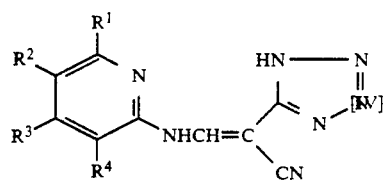

wherein $R^1$ through $R^4$ are as defined above, allowing an acid or a base to act on this compound to obtain a compound of the formula:

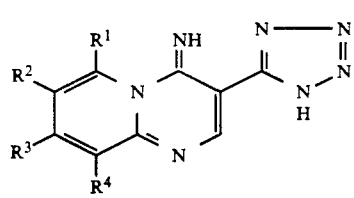

wherein $R^1$ through $R^4$ are as defined above, and then hydrolyzing the compound thus obtained.

The present invention also provides a process for producing a compound of the formula:

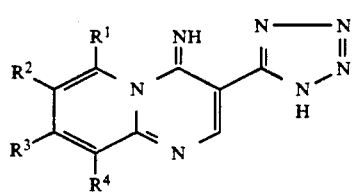

wherein $R^1$ through $R^4$ are as defined above, which comprises reacting a compound of the formula:

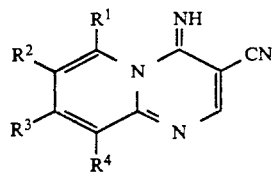

wherein $R^1$ through $R^4$ are as defined above, with hydrazoic acid.

The present invention further provides a process for producing a compound of the formula:

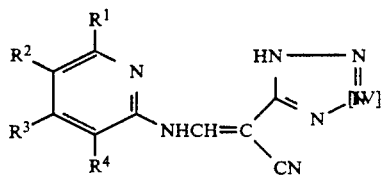

wherein $R^1$ through $R^4$ are as defined above, which comprises reacting a compound of the formula:

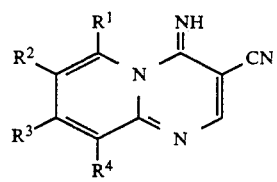

wherein $R^1$ through $R^4$ are as defined above, with a salt of hydrazoic acid.

The present invention still further provides a process for producing a compound of the formula:

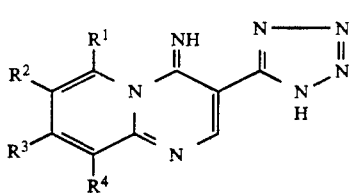

wherein $R^1$ through $R^4$ are as defined above, which comprises allowing an acid or a base to act on a compound of the formula:

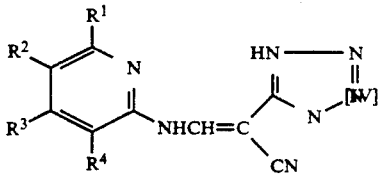

wherein $R^1$ through $R^4$ are as defined above.

The present invention also provides a compound of the formula:

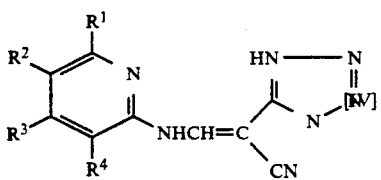

wherein $R^1$ through $R^4$ are as defined above.

The present invention further provides a compound of the formula:

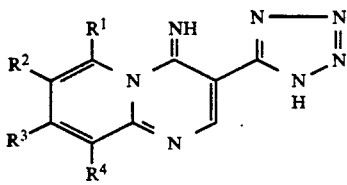

[II]

wherein $R^1$ through $R^4$ are as defined above.

DESCRIPTION OF THE PREFERRED EMBODIMENTS

According to the present invention, there is used a compound of the formula:

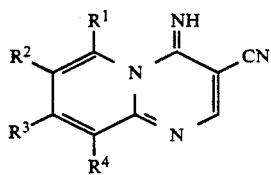

[III]

wherein $R^1$ and $R^3$ are independently a hydrogen atom or a lower alkyl group preferably having 1 to 6 carbon atoms; and $R^2$ and $R^4$ are independently a hydrogen atom, a halogen atom, a lower alkyl group preferably having 1 to 6 carbon atoms, a phenyl group, or

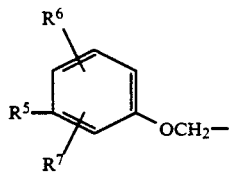

($R^5$ is a hydrogen atom or a hydroxyl group; $R^6$ is a hydrogen atom or an acyl group; and $R^7$ is a hydrogen atom, a lower alkyl group preferably having 1 to 6 carbon atoms or an allyl group) (hereinafter abbreviated as "compound [III]") as a starting material. The nitrile group of the compound [III] is converted to a tetrazole ring, whereby there is obtained a compound of the formula:

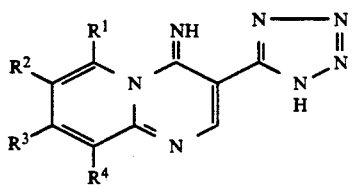

[II]

wherein $R^1$ through $R^4$ are as defined above (hereinafter abbreviated as "compound [II]") via or not via a compound of the formula [IV]:

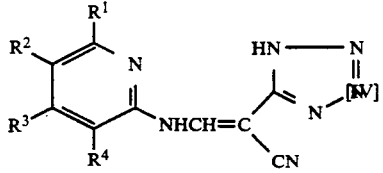

wherein $R^1$ through $R^4$ are as defined above (hereinafter abbreviated as "compound [IV]"). Then, the compound [II] is hydrolyzed to obtain a compound [I] of the formula:

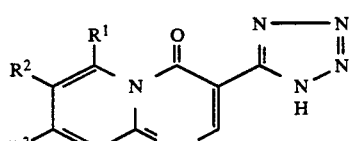

[I]

wherein $R^1$ through $R^4$ are as defined above. Thus, the present invention provides a production process which is much superior to conventional processes in all of yield, safety and workability.

In the compounds of the formulas [I] to [IV] of the present invention, $R^1$ and $R^3$ are independently a hydrogen atom or a lower alkyl group which may be linear or branched preferably having 1 to 6 carbon atoms (e.g. methyl group, ethyl group, propyl group, butyl group, amyl group, or hexyl group); and $R^2$ and $R^4$ are independently a hydrogen atom, a halogen atom (e.g. chlorine, bromine, fluorine or iodine), a lower alkyl group which may be linear or branched preferably having 1 to 6 carbon atoms (e.g. methyl group, ethyl group, propyl group, butyl group, amyl group, or hexyl group), a lower alkoxy group which may be linear or branched preferably having 1 to 6 carbon atoms (e.g. methoxy group, ethoxy group, propoxy group, butoxy group, amyloxy group, or hexyloxy group), a phenyl group, or

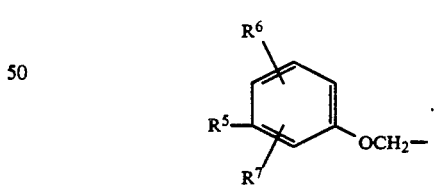

In the formula

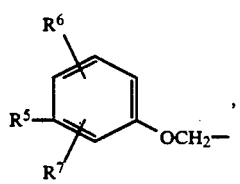

$R^5$ is a hydrogen atom or a hydroxyl group; $R^6$ is a hydrogen atom or an acyl group (e.g. acetyl group, propionyl group, butyryl group, or benzoyl group); and $R^7$ is a hydrogen atom, a lower alkyl group which may be linear or branched preferably having 1 to 6 carbon atoms (e.g. methyl group, ethyl group, propyl group, butyl group, amyl group or hexyl group), or an allyl group.

The production process of the present invention comprises substantially two steps, i.e., a step of converting the nitrile group of a compound [III] to a tetrazole ring to obtain a compound [II], and a step of hydrolyzing the compound [II] to convert its imino group to a ketone group.

The individual steps are explained below in detail.

Step of producing a compound [II] from a compound [III]

As a process for producing a compound [II] from a compound [III], there are (i) a process comprising reacting a compound [III] with hydrazoic acid to convert its nitrile group to a tetrazole ring, and thereby producing a compound [II] directly, and (ii) a process comprising reacting a compound [III] with a salt of hydrazoic acid to convert its nitrile group to a tetrazole ring for providing a compound [IV], and then allowing an acid or a base to act on the reaction product to obtain a compound [II].

In the conversion to a tetrazole ring in the process of (i), free hydrazoic acid may be used as it is or in the form of a solution such as aqueous solution, through there is usually employed a method comprising allowing an acid to act on a salt of hydrazoic acid in a reactor to liberate hydrazoic acid, in order to avoid dangers such as explosion, intoxication, etc.

The salt of hydrazoic acid used in the processes of (i) and (ii) includes various hydrazoic acid salts, for example, alkali metal salts such as sodium azide, potassium azide, etc.; alkaline earth metal salts such as calcium azide, magnesium azide, etc.; polyvalent metal salts such as aluminum azide, zinc azide, tin azide, etc.; ammonium azide; and salts of organic bases, such as trimethylammonium azide, aniline azide, etc. It is most preferable to use sodium azide singly which is the most easy to handle among commercially available hydrazoic acid salts and is not expensive. That is, when sodium azide is used alone in the production process of the present invention, the conversion to a tetrazole ring proceeds sufficiently under mild reaction conditions and a desired tetrazole product can be obtained in a short time in very high yield. Therefore, unlike in conventional processes, ammonium chloride, aluminum chloride or the like need not to be used together with sodium azide, so that all the above-mentioned problems caused by co-use of ammonium chloride or the like can be avoided.

As to the using amount of hydrazoic acid or a salt thereof, a theoretical amount or an amount somewhat larger than theoretical amount can give a sufficiently high yield, and hence remaining or generation of surplus or unnecessary hydrazoic acid can be suppressed as much as possible. Particularly when sodium azide is used alone, unnecessary hydrazoic acid is hardly generated, so that the problems such as air pollution are hardly caused.

In both the processes of (i) and (ii), the reaction temperature for the conversion to a tetrazole according to the present invention may usually be any temperature in the range of 0° C. to the reflux temperature of solvent for reaction. Although the reaction temperature is preferably high when it is desired to shorten the reaction time, the reaction proceeds sufficiently in a short time even at room temperature to give a product in high yield. Although the reaction time is, as matter of course, varied depending on the reaction temperature, a reaction time of several tens of minutes to several hours is usually sufficient in both the processes of (i) and (ii).

As a solvent for reaction used in the conversion to a tetrazole ring in the process of (i), any solvent may be used so long as it does not inhibit the conversion of the nitrile group to a tetrazole ring and is not affected in itself by hydrazoic acid or salts thereof. The solvent for reaction includes solvents such as alcohols (e.g. methanol, ethanol, etc.), ketones (e.g. acetone, methyl ethyl ketone, etc.), esters (e.g. methyl acetate, ethyl acetate, etc.), aromatic hydrocarbons (e.g. benzene, toluene, etc.), halogenated hydrocarbons (e.g. chloroform dichloromethane, etc.), ethers (e.g. tetrahydrofuran (THF), dioxane, diethylether, monoglymes, diglymes, etc.) acetonitrile, N,N-dimethylformamide (DMF), dimethylacetamide, dimethyl sulfoxide, hexamethylphosphoric triamide (HMPA), water, and the like, and acidic organic solvents such as acetic acid, formic acid and the like. These solvents may be used singly or as a proper mixture thereof. The solvent for reaction is not limited to these solvents and any solvent satisfying the above conditions can be used.

The kind of the acid used for liberating hydrazoic acid from the salt of hydrazoic acid in the process of (i) is not critical and includes, for example, mineral acids such as hydrochloric acid, sulfuric acid, nitric acid, etc.; and organic acids such as formic acid, acetic acid, benzenesulfonic acid, p-toluenesulfonic acid, methanesulfonic acid, etc. The using amount of said acid is an amount sufficient for liberating hydrazoic acid from the salt of hydrazoic acid. When there is used an acid which tends to have an undesirable influence on the conversion to a tetrazole ring, the using amount should be a minimum amount required for liberating hydrazoic acid. On the other hand, when there is used an acid such as acetic acid, formic acid or the like which is not liable to have an undesirable influence on the conversion to a tetrazole ring and functions as a solvent in itself, its using amount is not limited and other solvents need not be used together with such an acid.

After completion of the reaction, if necessary, the compound [II] is isolated by a conventional method, for example, collection of precipitated crystals by filtration after addition of water to the reaction mixture.

As a solvent for reaction used in the process of (ii), there can be exemplified all the solvents exemplified for the process of (i), except for the acidic organic solvents such as acetic acid, formic acid, etc.

In the process of (ii) a compound [IV] is obtained by the conversion to a tetrazole ring in a compound [III] and is a novel compound which has not been known in any literature.

Although the compound [IV] may be isolated, for example, by neutralizing the reaction solution after completion of the conversion to a tetrazole ring and collecting the precipitated crystals by filtration, it is also possible to carry out a subsequent ring-closing step by allowing an acid or a base to act directly on the reaction mixture without isolating the compound [IV].

In the process of (ii), the acid which is allowed to act on the compound [IV] includes protonic acids, for example, mineral acids such as hydrochloric acid, sulfuric acid, nitric acid, etc.; organic acids such as acetic acid, formic acid, benzenesulfonic acid, p-toluenesulfonic acid, methanesulfonic acid, etc.; and Lewis acids such as aluminum chloride, zinc chloride, tin tetrachloride, antimony hexafluoride, etc. The base which is allowed to act on the compound [IV] includes, for example, alkali hydroxides such as sodium hydroxide, potassium hydroxide; alkali carbonates such as sodium carbonate, potassium carbonate, etc.; metal alkoxides such as sodium methoxide, sodium ethoxide, etc.; ammonia; and organic bases such as pyridine, triethylamine, etc.

The step of ring closure by action of the acid or the base on the compound [IV] is carried out usually with heating, for example, at 60° to 100° C., and a reaction time of one to several hours is usually sufficient. In the case where the compound [IV] is isolated, water is usually used as solvent for reaction, but the solvent for reaction is not limited to water and the various solvents usable in the conversion to a tetrazole ring can, of course, also be used.

After completion of the reaction, water is added to the reaction mixture if necessary and then the resulting solution is neutralized, for example, with a mineral acid such as hydrochloric acid, sulfuric acid, nitric acid or the like, or an organic acid such as acetic acid, formic acid or the like to precipitate a compound [II] as crystals. The compound [II] is isolated by a conventional method, for instance, collection by filtration.

In the process of (i), when a portion of hydrazoic acid exists as a salt because the using amount of the acid is not sufficient for liberating hydrazoic acid, the conversion reactions to a tetrazole ring according to the processes of (i) and (ii) are carried out at the same time in the same system. Therefore, for converting a compound [IV] produced by the reaction of hydrazoic acid salt with a compound [III] to a compound [II], it becomes necessary to subject the whole reaction mixture to the ring-closing step using an acid or a base of the process of (ii).

Both of the compounds [II] thus obtained by the processes (i) and (ii) are novel compounds which have not been known in any literature.

Step of producing a compound [I] from a compound [II]

A compound [I] can easily be produced by hydrolyzing a compound [II] by a conventional method in water or an aqueous organic solvent such as aqueous methanol, aqueous ethanol, aqueous acetone, aqueous acetonitrile, aqueous THF, aqueous DMF or the like. Although the reaction proceeds at room temperature, the reaction is carried out usually with heating, for example, at 60° to 110° C. in order to shorten the reaction time. Similarly, in order to shorten the reaction time, there is added a mineral acid such as hydrochloric acid, sulfuric acid, nitric acid or the like, or an organic acid such as benzenesulfonic acid, p-toluenesulfonic acid, methanesulfonic acid or the like, as in conventional methods.

Although the compound [II] used may be an isolated one, it is also possible to use, as such, the reaction mixture obtained by the conversion to a tetrazole ring in a compound [III] (or a reaction mixture obtained by treating a compound [IV] with an acid or a base, in the case of the process in which the compound [II] is obtained via the compound [IV]). This means that a desired compound [I] can be obtained in one reactor without isolating an intermediate from the starting material [III]. Thus, there is given an embodiment which further enhances the usefulness of the present invention.

After completion of the hydrolysis, the compound [I] is isolated by a conventional method, for example, cooling followed by collection of the precipitated crystals by filtration.

In the production process of this invention described above, when any of the substituents $R^1$ through $R^7$ of the compounds [I] to [IV] is a functional group which requires protection under reaction, a step of introducing protecting group and a removing step should, of course, be properly incorporated.

The compound [III] used as a starting material in the present invention can easily be obtained, for example, by reacting ethoxymethylenemalononitrile with a 2-aminopyridine derivative in a solvent such as ethanol at room temperature according to the method described in J. Org. Chem., 51, 2988-2994 (1986), etc., and it is sufficient that the compound [III] thus obtained is used.

It has been reported in the above reference that this compound [III] undergoes xantomerism in a solution and is thus capable of existing in a structure of the formula [IIIa] in which the pyrimidine ring is closed, and a structure of the formula [IIIb] in which the pyrimidine ring is opened:

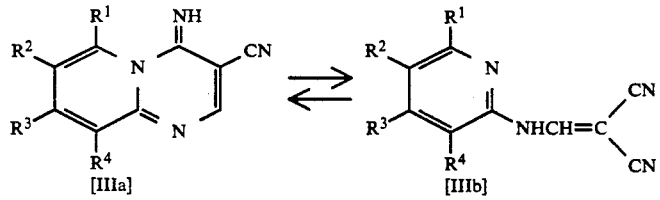

Therefore, the starting material used in this invention is also capable of existing in the above two forms of [IIIa] and [IIIb], but in the present specification, an explanation is given by assuming the structure of compound [III] to be [IIIa] for convenience.

Referential Examples and Examples are described below but they are not intended in any way to limit the scope of the present invention.

REFERENTIAL EXAMPLE 1

To 200 ml of ethanol were added 11.8 g (97 mmoles) of ethoxymethylenemalononitrile and 10.5 g (97 mmoles) of 2-amino-3-methylpyridine, and the reaction was carried out with stirring at room temperature for 2 hours. After completion of the reaction, the crystals precipitated were collected by filtration to obtain 13.5 g of 3-cyano-4-imino-9-methyl-4H-pyrido[1,2-a]pyrimidine. Yield: 76%.

M.p. 164°-166° C.

REFERENTIAL EXAMPLE 2

3-Cyano-4-imino-8-methyl-4H-pyrido[1,2-a]pyrimidine was obtained in exactly the same manner as in Referential Example 1 except for using 2-amino-4- methylpyridine in place of 2-amino-3-methylpyridine. Yield: 86%.

M.p. 204°–206° C.

REFERENTIAL EXAMPLE 3

3-Cyano-4-imino-7-methyl-4H-pyrido[1,2-a]pyrimidine was obtained in exactly the same manner as in Referential Example 1 except for using 2-amino-5-methylpyridine in place of 2-amino-3-methylpyridine. Yield: 81%.

M.p. 183°–185° C.

REFERENTIAL EXAMPLE 4

3-Cyano-4-imino-7-chloro-4H-pyrido[1,2-a]-pyrimidine was obtained in exactly the same manner as in Referential Example 1 except for using 2-amino-5-chloropyridine in place of 2-amino-3-methylpyridine. Yield: 72%.

M.p. 227°–228° C.

REFERENTIAL EXAMPLE 5

3-Cyano-4-imino-4H-pyrido[1,2-a]pyrimidine obtained in exactly the same manner as in Referential Example 1 except for using 2-aminopyridine in place of 2-amino-3-methylpyridine. Yield: 79%.

M.p. 172°–175° C.

REFERENTIAL EXAMPLE 6

3-Cyano-4-imino-9-phenoxymethyl-4H-pyrido[1,2-a]pyrimidine was obtained in exactly the same manner as in Referential Example 1 except for using 2-amino-3-phenoxymethylpyridine in place of 2-amino-3-methylpyridine. Yield: 72%.

M.p. 175° C.

REFERENTIAL EXAMPLE 7

3-Cyano-4-imino-9-[(4-acetyl-3-hydroxy-2-n-propylphenoxy)methyl]-4H-pyrido[1,2-a]pyrimidine was obtained in exactly the same manner as in Referential Example 1 except for using 2-amino-3-[(4-acetyl-3-hydroxy-2-n-propylphenoxy)methyl]pyridine in place of 2-amino-3-methylpyridine. Yield: 77%.

M.p. 174° C.

REFERENTIAL EXAMPLE 8

3-Cyano-4-imino-9-[(4-isopropylphenoxy)methyl]-4H-pyrido[1,2-a]pyrimidine was obtained in exactly the same manner as in Referential Example 1 except for using 2-amino-3-[(4-isopropylphenoxy)methyl]pyridine in place of 2-amino-3-methylpyridine. Yield: 42%.

M.p. 130°–132° C.

EXAMPLE 1

To 100 ml of HMPA were added 10.0 g (54.3 mmoles) of 3-cyano-4-imino-9-methyl-4H-pyrido[1,2-a]-pyrimidine and 3.53 g (54.3 mmoles) of sodium azide, and the reaction was carried out with stirring at 70° C. for 3 hours. After cooling, the reaction mixture was neutralized with diluted hydrochloric acid, and the crystals precipitated were collected by filtration to obtain 9.8 9 of light-brown power of 3-(3-methyl-2-pyridyl)amino-2-(1H-tetrazol-5-yl)-2-propenonitrile. Yield: 79%.

M.p. 191° C. (decomp.).

IR (KBr): 3050 cm$^{-1}$, 2220 cm$^{-1}$, 1630 cm$^{-1}$.

$^1$H-NMR δ ppm (DMSO-d$_6$): 10.97(d, 1H, NHCH=C). 8.79(d, 1H, 4-H), 7.11(dd, 1H, 5-H), 3 18(s, 1H, NHN=N—N), 2.41(s, 3H, CH$_3$)

MS (m/e): 227 (M+).

EXAMPLE 2

To 100 ml of DMF were added 10.0 g (54.3 mmoles) of 3-cyano-4-imino-9-methyl-4H-pyrido[1,2-a]pyrimidine and 3.53 g (54.3 mmoles) of sodium azide, and the reaction was carried out with stirring at 70° C for 3 hours. After cooling, the reaction mixture was neutralized with diluted hydrochloric acid, and the crystals precipitated were collected by filtration to obtain 9.1 g of light-brown powder of 3-(3-methyl-2-pyridyl)amino-2-(1H-tetrazol-5-yl)-2-propenonitrile. Yield: 73%.

EXAMPLE 3

To 100 ml of methanol were added 10.0 g (54.3 mmoles) of 3-cyano-4-imino-9-methyl-4H-pyrido[1,2-a]pyrimidine and 3.53 g (54.3 mmoles) of sodium azide and the reaction wa carried out with refluxing and stirring for 3 hours. After cooling, the reaction mixture was neutralized with diluted hydrochloric acid, and the crystals precipitated were collected by filtration to obtain 9.5 g of light-brown powder of 3-(3-methyl-2-pyridyl)amino-2-(1H-tetrazol-5-yl)-2-propenonitrile. Yield: 77%.

EXAMPLE 4

To 100 ml of water were added 10.0 g (54.3 mmoles) of 3-cyano-4-imino-9-methyl-4H-pyrido[1,2-a]pyrimidine and 3.53 g (54.3 mmoles) of sodium azide, and the reaction was carried out with stirring at 70° C. for 6 hours. After cooling, the reaction mixture was neutralized with diluted hydrochloric acid, and the crystals precipitated were collected by filtration to obtain 7.5 g of light-brown powder of 3-(3-methyl-2-pyridyl)amino-2-(1H-tetrazol-5-yl)-2-propenonitrile. Yield: 60%.

EXAMPLE 5

To 60 ml of acetic acid were added 10.0 g (54.3 mmoles) of 3-cyano-4-imino-9-methyl-4H-pyrido[1,2-a]pyrimidine and 3.53 g (54.3 mmoles) of sodium azide, and the reaction was carried out with stirring at 115° C. for 1 hour. After cooling, water was added to the reaction mixture, and the crystals precipitated were collected by filtration to obtain 13.5 g of light-brown powder of 4-imino-9-methyl-3-(1H-tetrazol-5-yl)-4H-pyrido[1,2-a]pyrimidine. Yield: 86%.

M.p. 233° C. (decomp.).

IR (KBr): 3400 cm$^{-1}$, 1695 cm$^{-1}$.

$^1$H-NMR δppm (CF$_3$COOD) 9.66(s, 1H, 2-H), 9 23(d, 1H, 6-H), 8.22(d, 1H, 8-H), 7.79(t, 1H, 7-H), 2.81(s, 3H, CH$_3$).

MS (m/e): 227 (M+).

EXAMPLE 6

To 20 ml of 1N hydrochloric acid was added 2.0 g (10.9 mmoles) of 3-(3-methyl-2-pyridyl)amino-2-(1H-tetrazol-5-yl)-2-propenonitrile, and the reaction was carried out with stirring at 100° C. for 1 hour. After cooling, the crystals precipitated were collected by filtration to obtain 1.7 g of light-brown powder of 4-imino-9-methyl-3-(1H-tetrazol-5-yl)-4H-pyrido[1,2-a]pyrimidine. Yield: 85%.

M.p. 236° C. (decomp.).

EXAMPLE 7

To 20 ml of 1N potassium hydroxide was added 2.0 g (10.9 mmoles) of 3-(3-methyl-2-pyridyl)amino-2-(1H-tetrazol-5-yl)-2-propenonitrile, and the reaction was carried out with stirring at 100° C. for 3.5 hours. After cooling, the reaction mixture was neutralized with hydrochloric acid, and the crystals precipitated were collected by filtration to obtain 1.78 g of light-brown powder of 4-imino-9-methyl-3-(1H-tetrazol-5-yl)-4H-pyrido[1,2-a]pyrimidine. Yield: 89%.

M.p. 239° C. (decomp.).

EXAMPLE 8

To 25 ml of 1N hydrochloric acid was added 0.95 g (4.2 mmoles) of 4-imino-9-methyl-3-(1H-tetrazol-5-yl)-4H-pyrido[1,2-a]pyrimidine, and the reaction was carried out with stirring at 80° C. for 3.5 hours. After cooling, the crystals precipitated were collected by filtration to obtain 0.85 g of light-brown crystals of 9-methyl-3-(1H-tetrazol-5-yl)-4H-pyrido[1,2-a]pyrimidin-4-one. Yield: 89%.

M.p. 277° C. (decomp.).

EXAMPLE 9

To 60 ml of acetic acid were added 10.0 g (54.3 mmoles) of 3-cyano-4-imino-9-methyl-4H-pyrido[1,2-a]pyrimidine and 3.53 g (54.3 mmoles) of sodium azide, and the reaction was carried out with stirring at 115° C. for 1 hour. Then, 15 ml of concentrated hydrochloric acid was added and the resulting mixture was subjected to reaction with stirring at 100° C. for 2 hours. After cooling, the crystals precipitated were collected by filtration to obtain 9.1 g of light-brown powder of 9-methyl-3-(1H-tetrazol-5-yl)-4H-pyrido[1,2-a]pyrimidin-4-one. Yield: 75%. M.p. 281° C. (decomp.).

EXAMPLE 10

To 80 ml of water were added 10.0 g (54.3 mmoles) of 3-cyano-4-imino-9-methyl-4H-pyrido[1,2-a]pyrimidine, 3.53 g (54.3 mmoles) of sodium azide and 5.5 g (54 mmoles) of concentrated hydrochloric acid, and the reaction was carried out with stirring at room temperature for 3 hours. Then, 5.5 g of concentrated hydrochloric acid was added and the resulting mixture was subjected to reaction with stirring at 90° C. for 1 hour. After cooling, the crystals precipitated were collected by filtration to obtain 9.1 g of light-brown powder of 9-methyl-3-(1H-tetrazol-5-yl)-4H-pyrido[1,2-a]pyrimidin-4-one. Yield: 73%. M.p. 288° C. (decomp.).

EXAMPLE 11

8-Methyl-3-(1H-tetrazol-5-yl)-4H-pyrido[1,2-a]pyrimidin-4-one was obtained in exactly the same manner as in Example 9 except for using 3-cyano-4-imino-8-methyl-4H-pyrido[1,2-a]pyrimidine in place of 3-cyano-4-imino-9-methyl-4H-pyrido[1,2-a]pyrimidine. Yield: 81%. M.p. 299° C. (decomp.).

EXAMPLE 12

7-Methyl-3-(1H-tetrazol-5-yl)-4H-pyrido[1,2-a]pyrimidin-4-one was obtained in exactly the same manner as in Example 9 except for using 3-cyano-4-imino-7-methyl-4H-pyrido[1,2-a]pyrimidine in place of 3-cyano-4-imino-9-methyl-4H-pyrido[1,2-a]pyrimidine. Yield: 87%. M.p. 305° C. (decomp.).

EXAMPLE 13

7-Chloro-3-(1H-tetrazol-5-yl)-4H-pyrido[1,2-a]pyrimidin-4-one was obtained in exactly the same manner as in Example 9 except for using 3-cyano-4-imino-7-chloro-4H-pyrido[1,2-a]pyrimidine in place of 3-cyano-4-imino-9-methyl-4H-pyrido[1,2-a]pyrimidine. Yield: 84%. M.p. 295° C. (decomp.).

EXAMPLE 14

3-(1H-Tetrazol-5-yl)-4H-pyrido[1,2-a]pyrimidin-4-one was obtained in exactly the same manner as in Example 9 except for using 3-cyano-4-imino-4H-pyrido[1,2-a]pyrimidine in place of 3-cyano-4-imino-9-methyl-4H-pyrido[1,2-a]pyrimidine. Yield: 86%. M.p. 307° C. (decomp.).

EXAMPLE 15

4-Imino-9-phenoxymethyl-3-(1H-tetrazol-5-yl)-4H-pyrido[1,2-a]pyrimidine was obtained in exactly the same manner as in Example 5 except for using 3-cyano-4-imino-9-phenoxymethyl-4H-pyrido[1,2-a]pyrimidine in place of 3-cyano-4-imino-9-methyl-4H-pyrido[1,2-a]pyrimidine. Yield: 61%.

M.p. 270° C. (decomp.).

IR (KBr, cm$^{-1}$): 3400, 1690, 1600, 1320.

$^1$H-NMR (270 MHz, DMSO-d$_6$) δ ppm: 9.54(1H, s, 2-H), 9.13(1H, d, 6-H), 8.26(1H, d, 8-H), 7.86(1H, t, 7-H), 7.34(2H, t, 3',5'-H), 7.10(2H, d, 2',6'-H), 7.00(1H, t, 4'-H), 5.62(2H, s, C$\underline{H}_2$).

MS (m/s): 329.

EXAMPLE 16

4-Imino-9-[(4-acetyl-3-hydroxy-2-n-propylphenoxy)methyl]-3-(1H-tetrazol-5-yl)-4H-pyrido[1,2-a]pyrimidine was obtained in exactly the same manner as in Example 5 except for using 3-cyano-4-imino-9-[(4-acetyl-3-hyiroxy-2-n-propylphenoxy)methyl]-4H-pyrido[1,2-a]pyrimidine in place of 3-cyano-4-imino-9-methyl-4H-pyrido[1,2-a]pyrimidine. Yield: 98%.

M.p. 286° C. (decomp.).

IR (KBr, cm$^{-1}$) 3150, 1700, 1630, 1600, 1270.

$^1$H-NMR (270 MHz, CF$_3$COOD) δ ppm: 9.91(1H, s, 2-H), 9.13(1H, d, 6-H), 8.76(H, d, 8-H), 8.08(1H, t, 7-H), 7.92 (1H, d, 5'-H), 6.89(1H, d, 6'-H), 5.89(2H, s, OC$\underline{H}_2$), 2.90(2H, t, C$\underline{H}_2$CH$_2$CH$_3$), 2.28(3H, s, C$\underline{H}_3$CO), 1.69-1.77 (2H, m, CH$_2$C$\underline{H}_2$CH$_3$), 1.08(3H, t, C$\underline{H}_3$)

MS (m/s): 419.

EXAMPLE 17

4-Imino-9-[(4-isopropylphenoxy)methyl]-3-(1H-tetrazol-5-yl)-4H-pyrido[1,2-a]pyrimidine was obtained in exactly the same manner as in Example 5 except for using 3-cyano-4-imino-9-[(4-isopropylphenoxy)methyl]-4H-pyrido-[1,2-a]pyrimidine in place of 3-cyano-4-imino-9-methyl-4H-pyrido[1,2-a]pyrimidine. Yield: 62%.

M.p. 277° C. (decomp.).

IR (KBr, cm$^{-1}$): 3150, 1695, 1640, 1600, 1250.

$^1$H-NMR (270 MHz, CF$_3$COOD) δ ppm: 9.88(1H, s, 2-H), 9.07(1H, d, 6-H), 8.72(1H, d, 8-H), 8.02(1H, t, 7-H), 7.29(2H, d, 3',5'-H), 7.07 (2H, d, 2',6'-H), 5.81(2H, s, C$\underline{H}_2$), 2.91-2.96(1H, m, C$\underline{H}$), 1.28(6H, s, C$\underline{H}_3$×2).

MS (m/s): 361.

EXAMPLE 18

9-Phenoxymethyl-3-(1H-tetrazol-5-yl)-4H-pyrido-[1,2-a]pyrimidin-4-one was obtained in exactly the same manner as in Example 9 except for using 3-cyano-4-imino-9-phenoxymethyl-4H-pyrido[1,2-a]pyrimidine in place of 3-cyano-4-imino-9-methyl-4H-pyrido[1,2-a]pyrimidine. Yield: 75%.

M.p. 281° C. (decomp.).

EXAMPLE 19

9-[(4-Acetyl-3-hydroxy-2-n-propylphenoxy)methyl]-3-(1H-tetrazol-5-yl)-4H-pyrido[1,2-a]pyrimidin-4-one was obtained in exactly the same manner as in Example 9 except for using 3-cyano-4-imino-9-[(4-acetyl-3-hydroxy-2-n-propylphenoxy)methyl]-4H-pyrido[1,2-a]pyrimidine in place of 3-cyano-4-imino-9-methyl-4H-pyrido[1,2-a]pyrimidine. Yield: 98%.

M.p. 254° C. (decomp.).

EXAMPLE 20

9-[(4-Isopropylphenoxy)methyl]-3-(1H-tetrazol-5-yl)-4H-pyrido[1,2-a]pyrimidine-4-one was obtained in exactly the same manner as in Example 9 except for using 3-cyano-4-imino-9-[(4-isopropylphenoxy)methyl]-4H-pyrido[1,2-a]pyrimidine in place of 3-cyano-4-imino-9-methyl-4H-pyrido[1,2-a]pyrimidine. Yield: 82%.

M.p. 277° C. (decomp.).

The present invention provides a novel and very effective process for producing a pyrido[1,2-a]pyrimidine derivative of the formula [I] which is very useful as an antiallergy agent. The production process of the present invention is markedly effective in that according to it, a desired pyrido[1,2-a]pyrimidine derivative can be obtained easily in very high yield under mild reaction conditions. Particularly when the conversion of the nitrile group of a compound [III] to a tetrazole ring is carried out using sodium azide, said production process is more markedly effective because it is highly safe and hardly involves problems such as air pollution and industrial wastes. Moreover, according to the production process of the present invention, it is also possible to obtain a desired pyrido[1,2-a]pyrimidine derivative from a starting compound [III] in one reactor, and it can also be said to be a great advantage of the present invention that the starting material itself is also much easier to synthesize than those used in conventional processes.

What is claimed is:

1. A process for producing a compound of the formula:

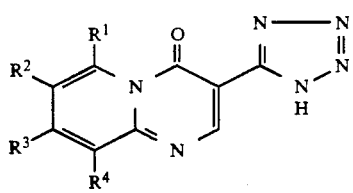

wherein $R^1$ and $R^3$ are independently a hydrogen atom or a lower alkyl group; and $R^2$ and $R^4$ are independently a hydrogen atom, a halogen atom, a lower alkyl group, a phenyl group or

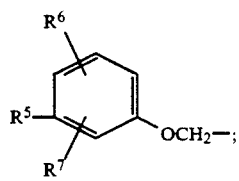

$R^5$ is a hydrogen atom or a hydroxyl group; $R^6$ is a hydrogen atom or an acetyl, propionyl, butyryl or benzoyl group; and $R^7$ is a hydrogen atom, a lower alkyl group, or an allyl group, which comprises reacting a compound of the formula:

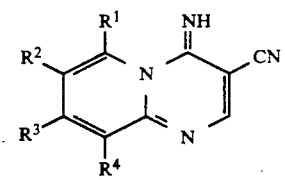

wherein $R^1$ through $R^4$ are as defined above, with hydrazoic acid to obtain a compound of the formula:

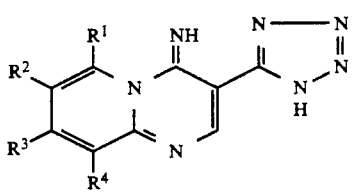

wherein $R^1$ through $R^4$ are as defined above, and then hydrolyzing the compound thus obtained.

2. A process for producing a compound of the formula:

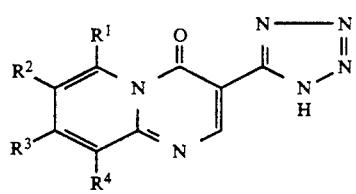

wherein $R^1$ and $R^3$ are independently a hydrogen atom or a lower alkyl group; and $R^2$ and $R^4$ are independently a hydrogen atom, a halogen atom, a lower alkyl group, a phenyl group, or

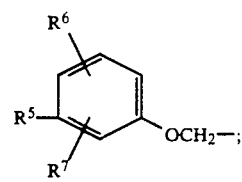

$R^5$ is a hydrogen atom or a hydroxyl group; $R^6$ is a hydrogen atom or an acetyl, propionyl, butyryl or benzoyl group; and $R^7$ is a hydrogen atom, a lower alkyl group, or an allyl group, which comprises reacting a compound of the formula:

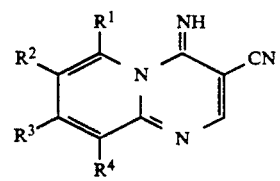

wherein $R^1$ through $R^4$ are as defined above, with a salt of hydrazoic acid to obtain a compound of the formula:

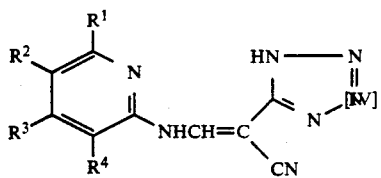

wherein $R^1$ through $R^4$ are as defined above, allowing an acid or a base to act on the compound of the formula [IV] to obtain a compound of the formula:

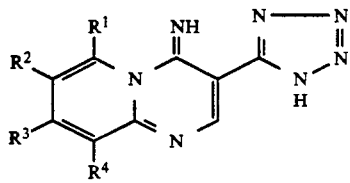

wherein $R^1$ through $R^4$ are as defined above, and then hydrolyzing the compound thus obtained.

3. A process according to claim 2, wherein the salt of hydrazoic acid is an alkali metal salt, alkaline earth metal salt, polyvalent metal salt, ammonium salt or salt of organic base, of hydrzoic acid.

4. A process according to claim 1, wherein $R^1$, $R^2$ and $R^3$ are hydrogen and $R^4$ is a lower alkyl group.

5. A process according to claim 1, wherein $R^1$, $R^2$ and $R^3$ are hydrogen; $R^4$ is a group of the formula

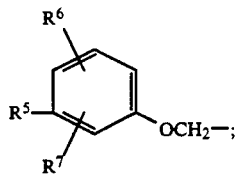

$R^5$ is hydrogen or a hydroxyl group; $R^6$ is hydrogen, an acetyl group, a propionyl group, a butyryl group, or a benzoyl group; and $R^7$ is a hydrogen atom, a lower alkyl group or an allyl group.

6. A process according to claim 2, wherein $R^1$, $R^2$ and $R^3$ are hydrogen and $R^4$ is a lower alkyl group.

7. A process according to claim 2, wherein $R^1$, $R^2$ and $R^3$ are hydrogen; $R^4$ is a group of the formula

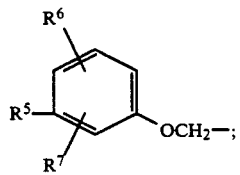

$R^5$ is hydrogen or a hydroxyl group; $R^6$ is a hydrogen atom, an acetyl group, a propionyl group, a butyryl group, or a benzoyl group; and $R^7$ is a hydrogen atom, a lower alkyl group or an allyl group.

* * * * *